(12) United States Patent
Frazer (10) Patent No.: US 8,066,657 B2
(45) Date of Patent: Nov. 29, 2011

(54) ABDOMINAL BINDER WITH IMPROVED DRAINAGE BULB HOLDING SYSTEM

(75) Inventor: Allison Frazer, Blackstone, MA (US)

(73) Assignee: Dale Medical Products, Inc., Plainville, MA (US)

( * ) Notice: Subject to any disclaimer, the term of this patent is extended or adjusted under 35 U.S.C. 154(b) by 0 days.

(21) Appl. No.: 12/020,971

(22) Filed: Jan. 28, 2008

(65) Prior Publication Data

US 2009/0192432 A1    Jul. 30, 2009

(51) Int. Cl.
  A61F 13/06    (2006.01)
  A61F 5/24    (2006.01)
  A61M 5/32    (2006.01)
  A61M 1/00    (2006.01)

(52) U.S. Cl. .......... 602/61; 128/95.1; 604/317; 604/174

(58) Field of Classification Search ................. 128/95.1, 128/96.1; 602/41, 60, 61; 604/317–327, 604/174
  See application file for complete search history.

(56) References Cited

U.S. PATENT DOCUMENTS

| | | | |
|---|---|---|---|
| 3,146,778 A | 9/1964 | Krawiec | |
| 3,161,199 A | 12/1964 | Sands | |
| 3,878,849 A | 4/1975 | Muller et al. | |
| 4,139,130 A | 2/1979 | Glusker et al. | |
| 4,435,171 A | 3/1984 | Goldberg et al. | |
| 4,445,894 A | 5/1984 | Kovacs | |
| 4,457,754 A | 7/1984 | Buttaravoli | |
| 4,511,358 A | 4/1985 | Johnson, Jr. et al. | |
| D282,694 S | 2/1986 | Gault | |
| 4,606,736 A | 8/1986 | Van De Weghe | |
| 4,665,566 A | 5/1987 | Garrow | |
| D290,306 S | 6/1987 | Pickens | |
| 4,738,661 A | 4/1988 | Marut | |
| 4,799,923 A * | 1/1989 | Campbell | 604/179 |
| 4,819,846 A | 4/1989 | Hannemann | |
| 4,821,736 A | 4/1989 | Watson | |
| 4,822,342 A | 4/1989 | Brawner | |
| 4,826,486 A | 5/1989 | Palsrok et al. | |
| 4,911,698 A | 3/1990 | Wapner | |
| 4,917,280 A | 4/1990 | Schneider | |
| 4,997,421 A | 3/1991 | Palsrok et al. | |
| 5,016,291 A | 5/1991 | Capper | |

(Continued)

FOREIGN PATENT DOCUMENTS

WO    WO 94/12231    6/1994

OTHER PUBLICATIONS

Declaration of Allison Frazer.

(Continued)

Primary Examiner — Patricia Bianco
Assistant Examiner — Tarla Patel
(74) Attorney, Agent, or Firm — Finnegan, Henderson, Farabow, Garrett & Dunner, LLP (57) ABSTRACT

An improved abdominal binder is provided. The abdominal binder can include at least one external securing mechanism for holding a drainage bulb. In one embodiment, the securing mechanism can include one or more strips of hook or loop type material. In another embodiment, an improved abdominal binder that can support multiple drainage bulbs externally of the abdominal binder is provided. The improved abdominal binder can further include one or more openings to receive a drainage tube of a bulb held external to the abdominal binder.

18 Claims, 7 Drawing Sheets

U.S. PATENT DOCUMENTS

| | | | |
|---|---|---|---|
| 5,048,512 A | 9/1991 | Turner et al. | |
| 5,053,027 A | 10/1991 | Manfredi | |
| 5,060,645 A | 10/1991 | Russell | |
| 5,087,251 A | 2/1992 | Heyman et al. | |
| 5,147,322 A | 9/1992 | Bowen et al. | |
| 5,234,420 A | 8/1993 | Horton et al. | |
| 5,244,464 A | 9/1993 | Madden et al. | |
| 5,263,941 A | 11/1993 | Cockrill | |
| 5,271,745 A | 12/1993 | Fentress et al. | |
| 5,284,469 A | 2/1994 | Jasen et al. | |
| D345,052 S | 3/1994 | Stokke et al. | |
| 5,305,742 A | 4/1994 | Styers et al. | |
| 5,320,097 A | 6/1994 | Clemens et al. | |
| 5,341,802 A | 8/1994 | Calebaugh | |
| 5,345,931 A | 9/1994 | Battaglia, Jr. | |
| 5,352,209 A | 10/1994 | Bird et al. | |
| 5,362,303 A | 11/1994 | Jasen et al. | |
| D354,812 S | 1/1995 | Jasen et al. | |
| 5,397,639 A | 3/1995 | Tollini | |
| 5,403,285 A | 4/1995 | Roberts | |
| 5,425,719 A | 6/1995 | Lessing, Jr. | |
| 5,433,359 A | 7/1995 | Flowers | |
| 5,468,229 A | 11/1995 | Chandler | |
| 5,468,231 A | 11/1995 | Newman et al. | |
| 5,480,719 A | 1/1996 | Tollini | |
| 5,496,282 A | 3/1996 | Militzer et al. | |
| 5,515,866 A | 5/1996 | Somers | |
| 5,643,236 A | 7/1997 | Hadley | |
| 5,669,884 A | 9/1997 | Bennes et al. | |
| 5,672,159 A | 9/1997 | Warrick | |
| 5,688,248 A | 11/1997 | Lessing, Jr. | |
| 5,709,665 A | 1/1998 | Vergano et al. | |
| 5,716,344 A | 2/1998 | Kiel | |
| 5,728,070 A | 3/1998 | Walker et al. | |
| D393,310 S | 4/1998 | Russo | |
| D395,151 S | 6/1998 | Maddox | |
| 5,776,105 A | 7/1998 | Corn | |
| 5,845,643 A | 12/1998 | Vergano et al. | |
| 5,853,396 A | 12/1998 | Bennes et al. | |
| 5,897,519 A * | 4/1999 | Shesol et al. | 602/79 |
| 5,941,856 A | 8/1999 | Kovacs et al. | |
| 5,941,859 A | 8/1999 | Lerman | |
| 5,961,501 A | 10/1999 | Cassidy et al. | |
| 5,968,072 A * | 10/1999 | Hite et al. | 606/202 |
| 5,980,498 A | 11/1999 | Brown et al. | |
| 5,980,499 A | 11/1999 | Ekey | |
| 6,045,542 A | 4/2000 | Cawood | |
| 6,126,639 A | 10/2000 | Sutherland et al. | |
| 6,129,709 A | 10/2000 | Millen | |
| D433,227 S | 11/2000 | Evans | |
| 6,152,915 A | 11/2000 | Watson et al. | |
| 6,165,168 A | 12/2000 | Russo | |
| 6,168,578 B1 | 1/2001 | Diamond | |
| 6,296,164 B1 * | 10/2001 | Russo | 224/602 |
| 6,379,327 B2 * | 4/2002 | Lundy | 604/74 |
| 6,419,660 B1 | 7/2002 | Russo | |
| 6,610,032 B1 * | 8/2003 | Prody | 604/179 |
| 7,284,729 B2 | 10/2007 | Walsh et al. | |
| 7,284,730 B2 | 10/2007 | Walsh et al. | |
| D595,416 S | 6/2009 | Kovacs et al. | |
| 2005/0181705 A1 * | 8/2005 | Maupin | 450/155 |
| 2008/0108948 A1 * | 5/2008 | Beaver | 604/179 |
| 2008/0221525 A1 * | 9/2008 | Manzano-Rivera | 604/179 |

OTHER PUBLICATIONS

Scardillo, "Postoperative Care of Patients with Surgical Drains", Perspectives: Recovery Strategies from the OR to Home, vol. 4, No. 4, 2006.

A-T Surgical Mfg: "Abdominal Binders," [online] http://web.archive.org/web/20040214021111/a-tsurgical.com/Merchant2/merchant.mv?Screen=CTGY&Store_Code=atscms&Category_Code=atsab, Jan. 28, 2004, retrieved from the internet Nov. 12, 2010.

Dale® Medical Products, Inc., "Abdominal Binder with Exclusive Stretch Material," brochure, 2002.

DonJoy, "Back Bracing," [online] http://web.archive.org/web/20080409135843/www.donjoy.com/index.asp/fuseaction/products.list/cat/8/, Jan. 16, 2008, retrieved from the internet Nov. 18, 2010.

FLA Orthopedics, Inc., "Premium Woven Surgical Binders, Paneled Service 34-630X (3-Panel 9") Series 34-640X (4-Panel 12")," [online] http://web.archive.org/web/20060921094420/flaorthopedics.com/srchproducts/abdominalsupports/abdominalbinder.htm Feb. 1, 2005, retrieved from the internet Nov. 12, 2010.

Frank Stubbs Company, Inc., "3-Panel, 9" Abdominal Binder (#1083)," [online] http://web.archive.org/web/20060509034247/www.fstubbs.com/products/1083.htm, Feb. 3, 2006, retrieved from the internet Nov. 12, 2010.

Golda, Inc., "Surgi-Binder," [online] http://web.archive.org/web/20070909140535/www.goldainc.com/prod.sbinder.html, Jan. 24, 2007, retrieved from the internet Nov. 12, 2010.

Tetramed, "Abdominal Binders," [online] http://web.archive.org/web/20021004043254/www.tetramed.com/cont01.htm, Aug. 8, 2002, retrieved from the internet Nov. 12, 2010.

* cited by examiner

ABDOMINAL BINDER WITH IMPROVED DRAINAGE BULB HOLDING SYSTEM

FIELD

The present disclosure relates to the field of abdominal binders, and more particularly, to abdominal binders equipped to hold drainage bulbs and other medical instruments.

BACKGROUND

In the course of many abdominal surgeries, patients will have a large incision across or along a significant part of the abdominal wall. The incision may pass through the supporting fascia, resulting in potential weakening of the abdominal wall. At the conclusion of the surgical operation, the incision is closed with sutures and/or staples. However, after the surgery, the area of the incision can cause significant pain. Further, this closure is typically not as strong, at least initially, as the original, uninterrupted abdominal fascia. Therefore, the region of incision provides a potentially weak area in which the abdominal wall may reopen, a process known as dehiscence, thereby causing pain and potential infection risk to a patient.

After surgery, additional abdominal support may be desirable to reduce pain and prevent dehiscence. One device typically used for abdominal support is an abdominal binder, which includes a flexible piece of cloth or elastic material that can be wrapped snuggly around the abdomen of the patient to provide support to the abdominal wall. Use of such abdominal binders helps to promote earlier ambulation, enhance pulmonary function, and alleviate incisional pain. A variety of different abdominal binders are known in the art. Such binders can be made from a number of different materials and can be secured to the patient's abdomen using a number of mechanisms.

In addition to abdominal binders, surgical patients may also have additional medical instruments that must be carried around for some time after surgery. For example, for some surgical patients it is necessary to provide drainage to a wound to remove fluid that may accumulate after surgery. Typically, drainage is provided through a drainage bulb, which can include a tube that extends into a wound and an external bulb that provides suction to the wound to collect fluid. These drainage bulbs must be supported through clips or tape that secure the bulbs to the patient's clothing or directly to the patient's skin. Further, patients with abdominal binders may secure a drainage bulb beneath the binder. However, the use of tape, pins, and clips can be inconvenient, and securing the drainage bulb beneath an abdominal binder can be uncomfortable. For example, as the drainage bulb begins to fill, the drainage bulb can become relatively bulky and can exert uneven pressure against the patient's skin. In addition, some patients need multiple drainage bulbs, and it may be difficult to secure multiple bulbs beneath a single abdominal binder.

Accordingly, there is a need for abdominal binders that provide improved mechanisms for securing drainage bulbs or other medical devices that may be used post operatively.

SUMMARY

In one exemplary embodiment consistent with principles of this disclosure, an improved abdominal binder is provided. The abdominal binder can include at least one external securing mechanism for holding a drainage bulb. In one embodiment, the securing mechanism can include one or more strips of hook or loop type material that can be attached to hook or loop material on a surface of the abdominal binder.

In another embodiment consistent with principles of this disclosure, an improved abdominal binder that can support multiple drainage bulbs externally of the abdominal binder is provided. In one embodiment, the abdominal binder includes a pocket affixed to the outside of the abdominal binder for holding one of more drainage bulbs. In another embodiment, the abdominal binder includes a sheet of material being attachable and reattachable to an external surface of the abdominal binder to secure a drainage bulb to the binder.

In another embodiment, an improved abdominal binder is provided. In this embodiment, the abdominal binder includes a mechanism for securing one or more drainage bulbs external to the abdominal binder as well as one or more openings in the abdominal binder wall to provide an inlet for a drainage bulb tube. In one embodiment, the one or more openings can include multiple, regularly-spaced openings in the abdominal binder wall.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated and constitute a part of this specification, provide exemplary embodiments of disclosure and, together with the description, serve to explain the principals of this disclosure.

DETAILED DESCRIPTION

Reference will now be made in detail to the exemplary embodiments, an examples of which are illustrated in the accompanying drawings. Wherever possible, the same reference numbers will be used throughout the drawings to refer to the same or like parts.

An improved abdominal binder is disclosed herein. The abdominal binder can be used by patients after a surgical operation. In addition, the abdominal binder can have improved systems for holding drainage bulbs and other devices external to the binder.

Figure 1:
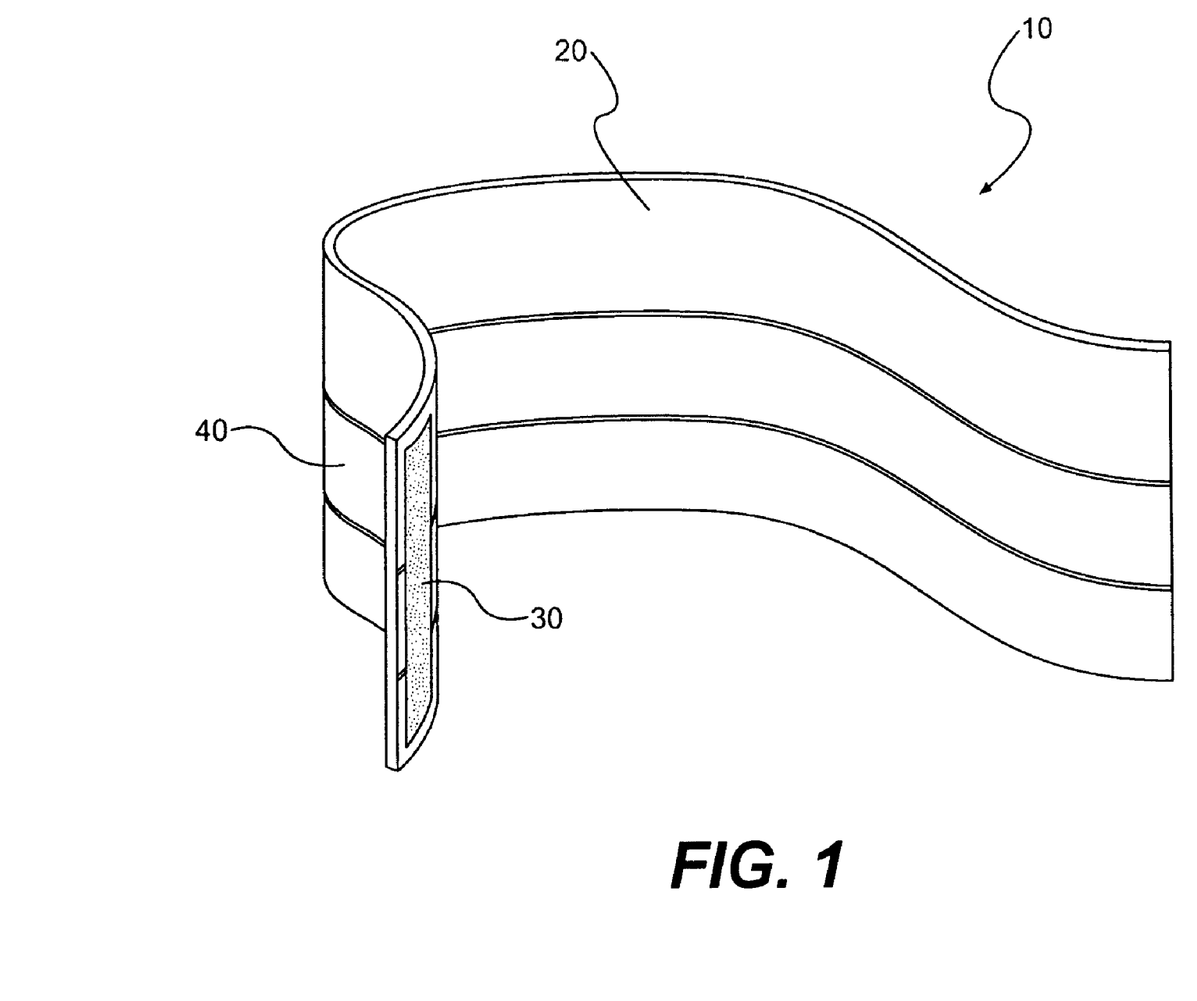
FIG. 1 illustrates an abdominal binder, according to one exemplary embodiment.
Figure 2:
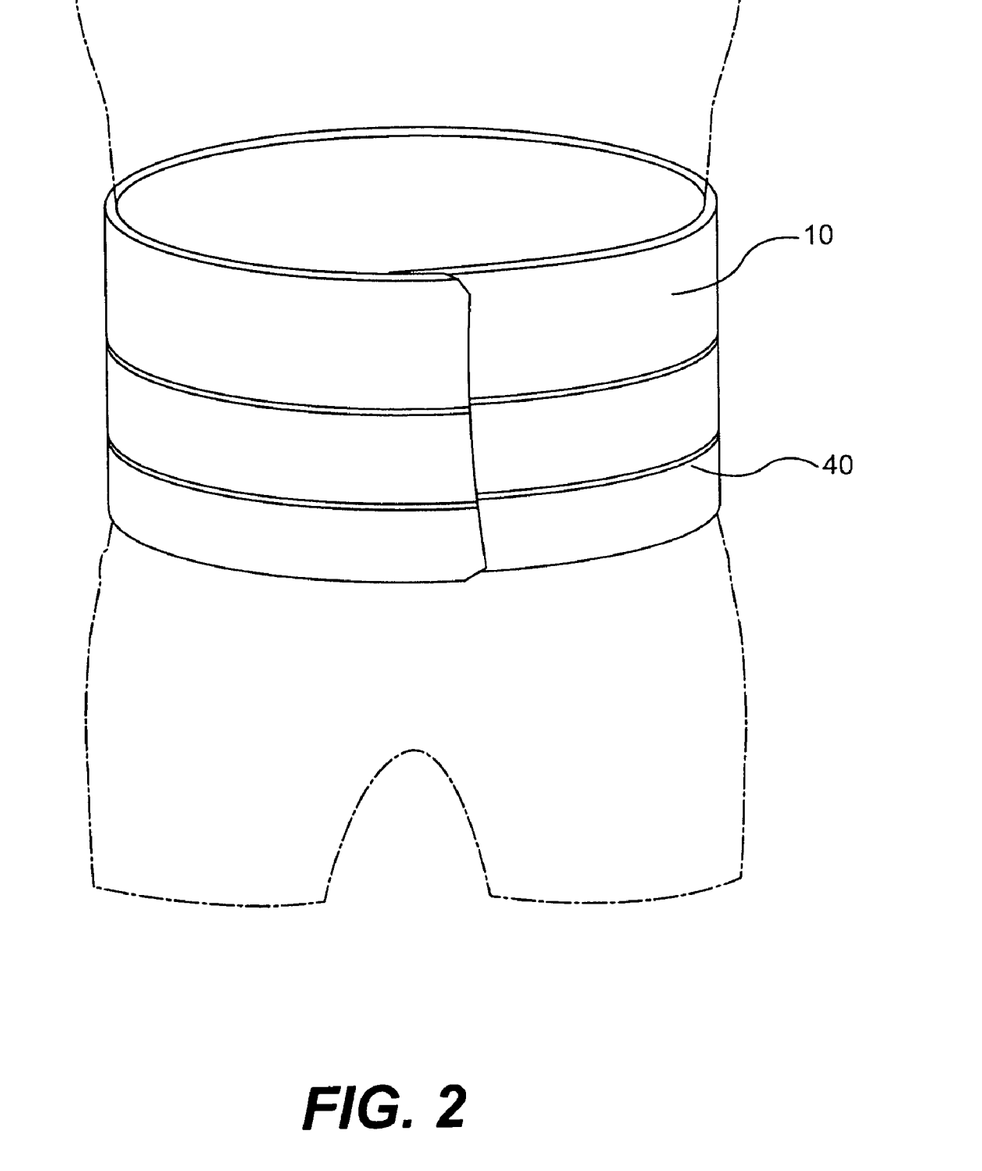
FIG. 2 illustrates the abdominal binder of FIG. 1 being worn by a patient.

FIG. 1 illustrates one abdominal binder, according to a exemplary disclosed embodiment. The abdominal binder 10 can include, for example, an elongate sheet 20 of soft, flexible material. Further, the abdominal can include mechanisms for securing the abdominal binder 10 to a patient. For example, in one embodiment the abdominal binder 10 can include hook and loop type fabric. As shown in FIG. 1, the elongate sheet 20 can include at least one surface 40 that includes a loop-pile type material. Further, the abdominal binder 10 can include at least one section 30 that includes a hook-type material. As shown in FIG. 2, when the abdominal binder 10 is wrapped around the abdomen of a patient, the loop-pile fabric on the first surface 40 of the abdominal binder 10 will contact the hook-type material section 30, thereby securing the abdominal binder 10 to the patient.

It will be appreciated that the abdominal binder 10 can be formed from a variety of different materials and can include a number of different mechanisms for securing the abdominal binder 10 to a patient. For example, the elongate sheet 20 of the abdominal binder 10 can include a variety of different soft, pliable materials. Suitable materials can include, for example, cotton, polyester, and a variety of additional synthetic or naturally-occurring materials. The specific materials can be selected for patient comfort, breathability, cost, and hygienic purposes. In addition, as noted above, the abdominal binder 10 can be secured to the patient using a variety of mechanisms including, for example, clips, tape, adhesives, hook-and-loop type fabric (e.g., Velcro™), and/or combinations of these attachment mechanisms or other attachment mechanisms known in the art.

As noted above, the abdominal binder of the present disclosure can include improved mechanisms for securing drainage bulbs and other medical instruments to the abdominal binder. In some embodiments, drainage bulbs can be secured to the external surface of an abdominal binder so that the drainage bulbs do not need to be held under the abdominal binder, thereby improving comfort and hygiene for the patient. Various embodiments of the disclosed abdominal binders are shown in FIGS. 3 through 8.

Figure 3:
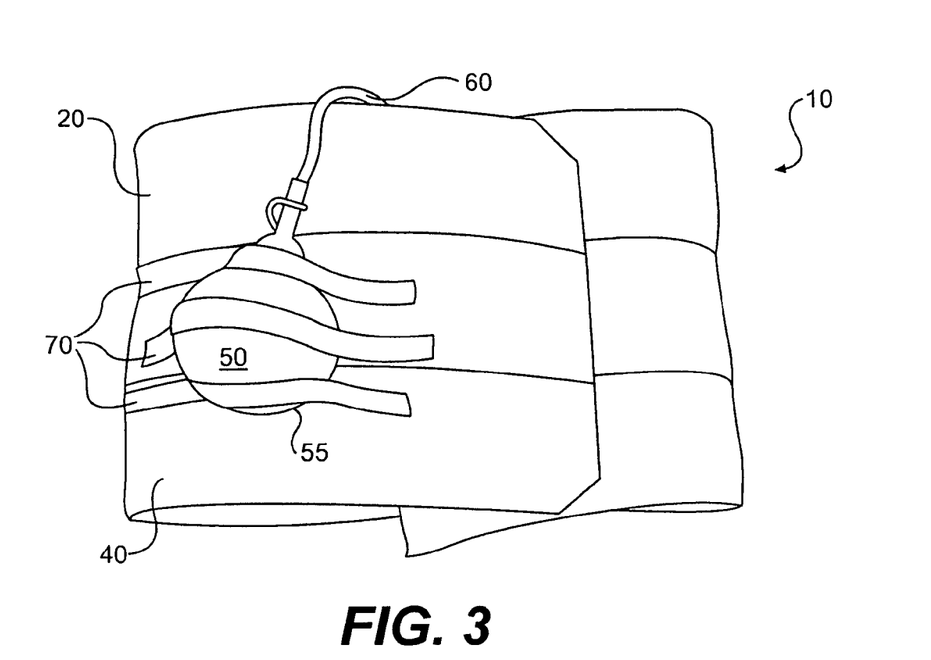
FIG. 3 illustrates an abdominal binder with an externally-secured drainage bulb, according to another exemplary embodiment.

FIG. 3 illustrates an abdominal binder with an externally-secured drainage bulb 50, according to one exemplary embodiment. As shown, the drainage bulb 50 can include a number of components and can further include a number of drainage bulb types. For example, as shown, the drainage bulb 50 includes a Jackson-Pratt bulb, which is commonly used in the art. However, any suitable drainage bulb type can be selected for use with the abdominal binders of the present disclosure. A typical Jackson-Pratt drainage bulb will include a main flexible bulb component 55 and a drainage tube 60. The bulb component 55 may be compressed and configured to apply suction to the drainage tube 60, thereby allowing fluid or debris to be removed from an incision after surgery. The drainage tube 60 may be secured to a surgical incision that is at least partially contained under the abdominal binder 10, as worn by the patient. Further, as shown, the drainage tube 60 can be looped over the top or bottom margin of the abdominal binder 10 to access a surgical site.

As shown, the abdominal binder 10 can include one or more strips 70 for securing the drainage bulb 50 to the external surface of the abdominal binder 10. For example, as shown in FIG. 3, the abdominal binder 10 includes three elongated strips 70 that are configured to secure the drainage bulb 50 to the external surface 40 of the abdominal binder 10. In one embodiment, the strips 70 can include at least one surface that includes a hook-type material that may be attached to loop-type fabric contained on an external surface 40 of the abdominal binder 10. Further, the abdominal binder 10 can include other mechanisms for securing the strips 70 to the abdominal binder to allow the drainage bulb 50 to be held thereto. For example, the strips 70 can include attachable and detachable adhesives, clips, and/or any other suitable attachment mechanisms known in the art. In addition, it will be understood that multiple drainage bulbs 50 can be secured to the external surface 40 using longer or additional strips.

Figure 4:
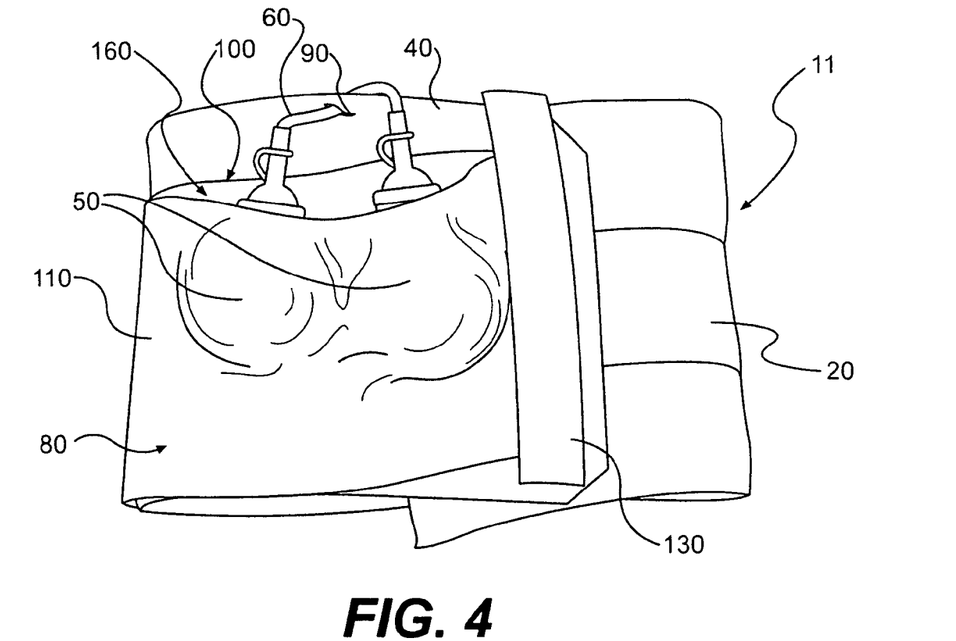
FIG. 4 illustrates another embodiment of an abdominal binder of the present disclosure including multiple externally-held drainage bulbs.

FIG. 4 illustrates another embodiment of an abdominal binder of the present disclosure. In some embodiments, it may be desirable to provide an abdominal binder 11 that includes a system for holding multiple drainage bulbs on an exterior portion of the abdominal binder 11, as shown in FIG. 4. The abdominal binder 11 of FIG. 4 is similar to the abdominal binder 10, as shown in FIGS. 1 through 3. The abdominal binder 11 again includes an elongate sheet 20 of soft, flexible material, and further includes a mechanism for securing the abdominal binder 11 to the patient, such as hook-and-loop type material (e.g., Velcro™). Further, the abdominal binder 11 includes a pouch system 80 for securing multiple drainage bulbs 50 to the external surface 40 of the abdominal binder 11, thereby providing improved patient comfort by preventing the need for securing the multiple drainage bulbs 50 beneath the abdominal binder 11. The pouch system 80 can be formed from soft, flexible fabric similar to that used to produce abdominal binder sheet 20. The pouch can be formed from two sheets of material, including a forward sheet 110 and a back sheet 100. The sheets 100, 110 can be attached to one another at end regions 130, thereby forming a pocket 160 between the sheets 110, 100.

As shown in FIG. 4, the pouch system 80 can be secured to the abdominal binder at end regions 130. In some embodiments, it may be desirable to attach the pouch system 80 using an attachable/detachable mechanism. For example, in one embodiment, the end regions 130 can include a hook-type fabric that can attach to the external surface 40 of abdominal binder 11 including a loop-pile fabric. Further, in other embodiments, the pouch system 80 can be attached to the abdominal binder 11 with a permanent mechanism. Such permanent attachment mechanisms can include, for example, stitches, clips, staples, permanent adhesives, and any other permanent attachment mechanism known in the art.

In addition, the abdominal binder 11 illustrates another aspect of the improved abdominal binders of the present disclosure. As shown in FIG. 4, the drainage bulbs 50 include drainage tubes 60 that must be inserted into a wound contained beneath the abdominal binder 11. In some embodiments, the drainage tube 60 can be looped over a top or bottom margin of the abdominal binder to access the region of the abdominal wall behind the abdominal binder 11. However, this may be inconvenient or uncomfortable for some patients, especially when multiple drainage bulbs are used. Therefore, the improved abdominal binders of the present disclosure can include one or more openings 90 configured to receive a drainage bulb tube 60 to allow access to a wound contained under the abdominal binder. As described in detail below with reference to FIG. 6, the openings 90 can be spaced at multiple positions along the abdominal binder material 20, thereby allowing the drainage tubes 60 to access surgical locations contained at a variety of different positions under the abdominal binder.

Figure 5:
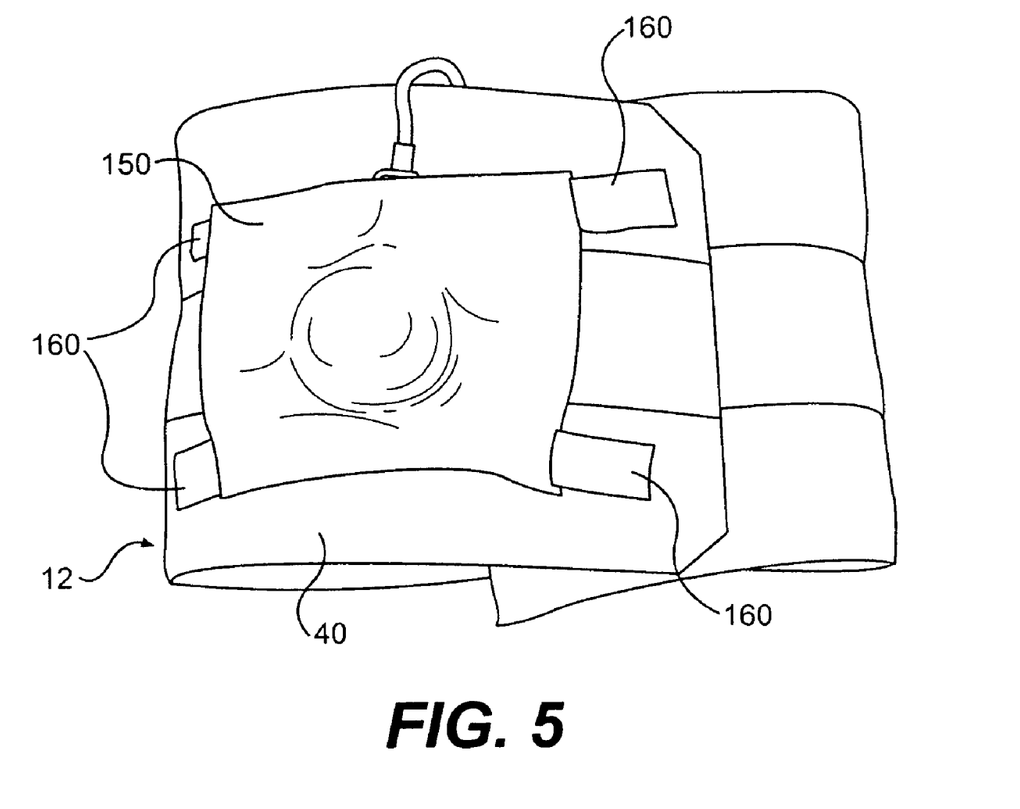
FIG. 5 illustrates another embodiment of an abdominal binder including an externally-secured drainage bulb.

FIG. 5 illustrates another embodiment of the improved abdominal binders of the present disclosure. As shown, the abdominal binder 12 of FIG. 5 includes a single sheet of material 150 that may be used to secure one or more drainage bulbs 50 to the external surface 40 of the abdominal binder 12. Further, the sheet 150 can include one or more attachment mechanisms 160 located on the perimeter of the sheet 150. The attachment mechanisms 160 can include, for example, attachable/reattachable mechanisms, such as hook-type fabric attachable to loop-pile Velcro fabric contained on the external surface 40 of the abdominal binder 12. The attachable and reattachable mechanisms 160 can allow a drainage bulb to be secured at a variety of selected locations on the external surface 40 of the abdominal binder 12. Further, the attachable and reattachable mechanisms 160 can secure drainage bulbs that vary in sizes and number to be attached to the external surface 40 of the abdominal binder 12. The sheet 150 can be constructed from a variety of different materials including various natural and synthetic cloth or elastic materials.

Figure 6:
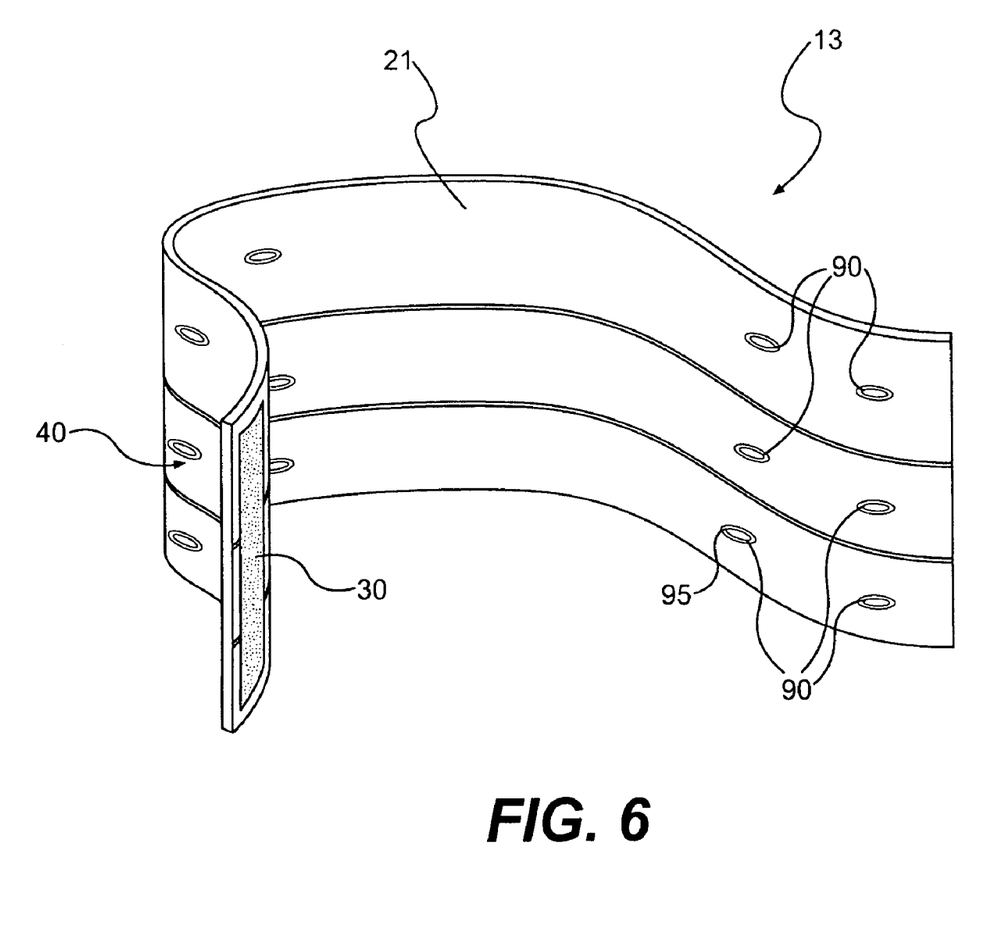
FIG. 6 illustrates another embodiment of an abdominal binder including multiple openings in the abdominal binder wall.

As noted previously, the abdominal binders of the present disclosure can include one or more openings configure to receive a drainage tube 60 of a drainage bulb 50 to allow the drainage tube 60 to access a surgical location contained beneath the abdominal binder. For example, as shown in FIG. 6, the abdominal binder 13 includes multiple openings 90 positioned at various locations along the abdominal binder material 21. These openings 90 can be positioned at a sufficient number of locations to allow the drainage tube 60 to access virtually any location beneath the abdominal binder 13. Further, in some embodiments, the openings 90 can include a reinforced perimeter region 95. Since the abdominal binder 13 may be produced from a soft, flexible material, the openings 90 could potentially create an area of weakening in the fabric. Therefore, to prevent tearing at the regions of the opening 90 when pressure is exerted by the drainage tube 60, the perimeter 95 of the openings 90 can be reinforced with additional fabric or stitching. It should be noted that these openings 90 can be used with any of the attachment mechanisms described previously with references to FIGS. 3-5 when securing drainage bulbs to an external surface of an abdominal binder.

Figure 7:
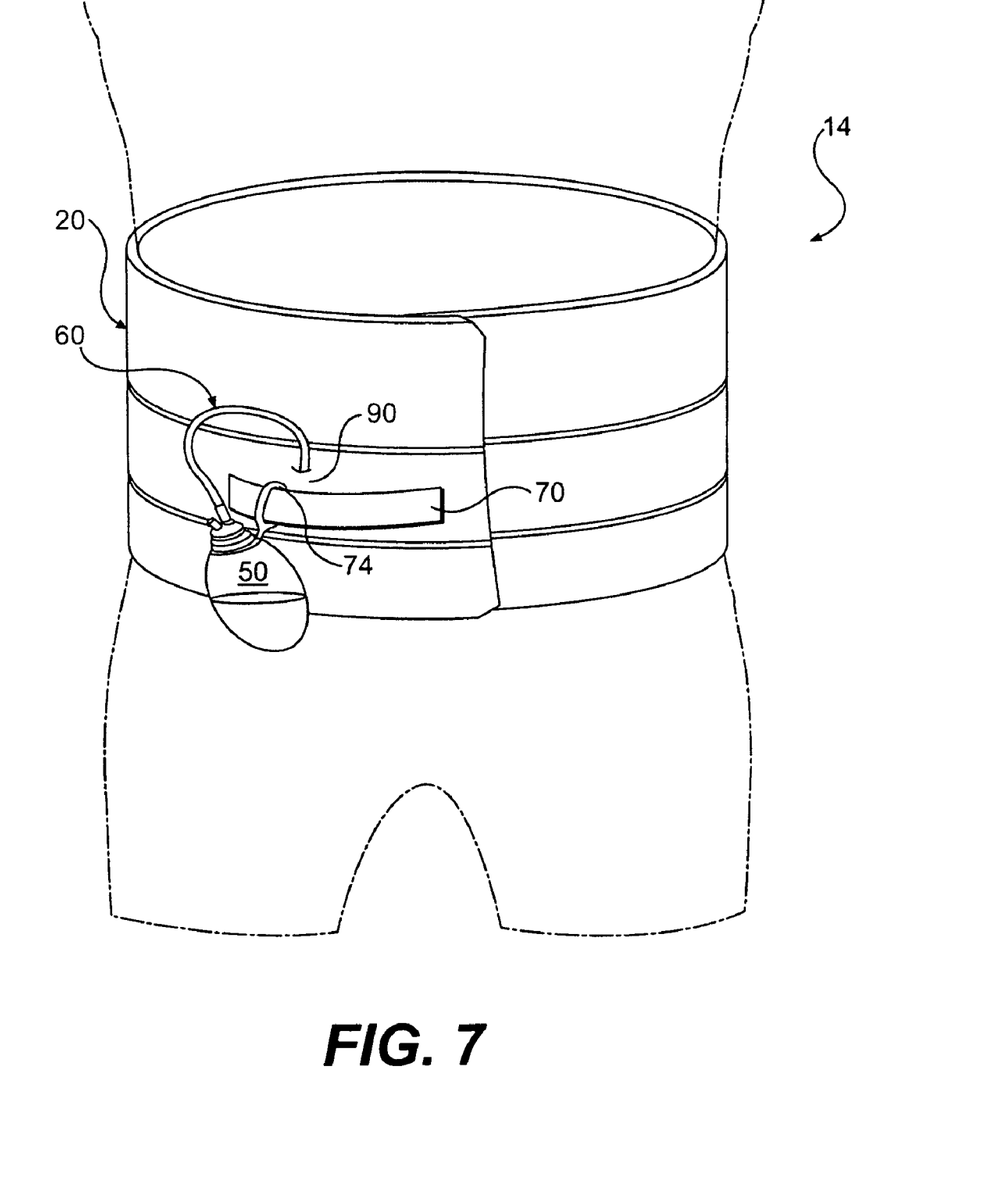
FIG. 7 illustrates an abdominal binder with an externally-secured drainage bulb, according to another exemplary embodiment.

FIG. 7 illustrates an abdominal binder 14 with an externally-secured drainage bulb, according to another exemplary embodiment. As shown, the binder 14 is similar to the binder 10 of FIG. 3, including a sheet 20 of flexible material configured to be secured around a patient's abdomen. The binder can further include one or more openings 90 to receive a tube 60 of a drainage bulb 50.

The bulb 50 can be secured external to the sheet 20 via a strip 70. The strip may include hook or loop material configured to be removably attached to the surface of the sheet 20. Further, the bulb 50 can be secured to the strip 70 via a flexible loop 74. The loop 74 may be permanently or removably attached to the bulb 50, and the strip 70 can be passed through the loop 74 to secure the bulb 50 to the abdominal binder. Further, multiple bulbs can be attached in this manner using a single strip 70, or multiple strips disposed at different locations on the binder 10.

Figure 8:
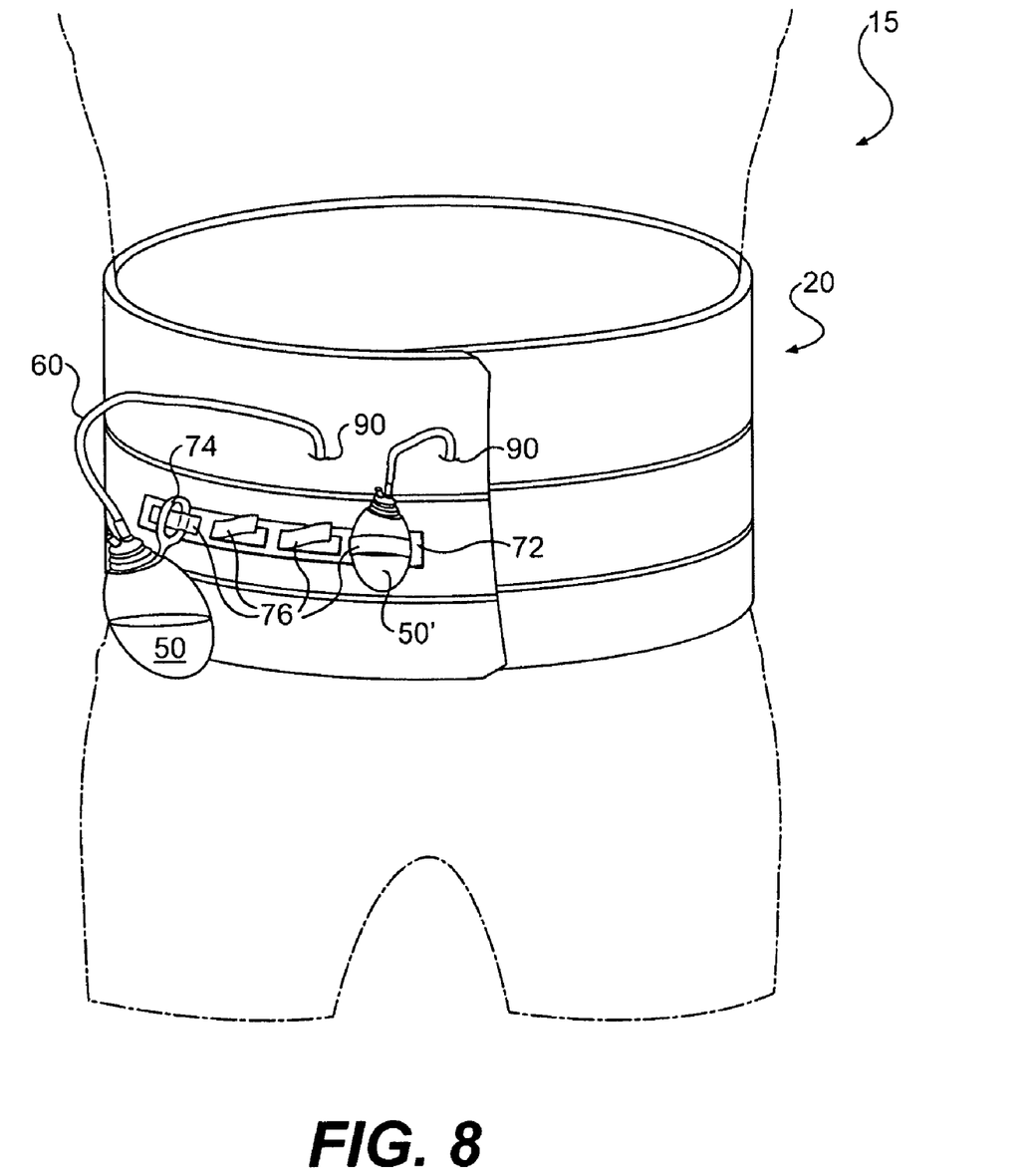
FIG. 8 illustrates another embodiment of an abdominal binder of the present disclosure including multiple externally-held drainage bulbs.

FIG. 8 illustrates another embodiment of an abdominal binder 15 of the present disclosure including multiple externally-held drainage bulbs 50, 50'. As shown, the abdominal binder 15 can include one or more strips 72 for securing the drainage bulbs 50, 50' to the external surface of the abdominal binder 15. Similar to the strip 70 of FIG. 3, the strip 72 can include at least one surface that includes a hook-type material that may be attached to loop-type fabric contained on an external surface of the abdominal binder 15. In addition, the strip 72 can include one or more tabs 76 configured to secure the drainage bulbs 50. For example, as shown, the strip 72 includes four tabs 76 that have been die-cut in a single piece of hook-type material, and each tab 76 can be repeatedly attached to, removed from, and reattached to the binder sheet 20.

As shown in FIG. 8, the strip 72 can secure multiple drainage bulbs. For example, as shown, a drainage bulb 50 having a loop 74, as described with reference to FIG. 7, can be secured by passing a tab 76 through the loop 74. Alternatively, or additionally, a drainage bulb 50' can be secured to the external surface of the binder sheet 20 by securing the hook-type material of a tab 76 over the bulb 50'. Multiple bulbs may be secured using one or both of these methods.

It will be apparent to those skilled in the art that various modifications and variations can be made consistent with the present disclosure. For example, various features within several embodiments disclosed herein can be combined with features from other abdominal binder assembly embodiments. Further, although described particularly for securing drainage bulbs to an external surface of an abdominal binder, it will be appreciated that the securing mechanisms of the present disclosure can be used to secure other devices to an external surface of abdominal binders. Other embodiments consistent with abdominal binders will be apparent to those skilled in the art from consideration of the specification and practice of the disclosure. It is intended that the specification and examples be considered as exemplary only with the true scope and spirit of disclosure being indicated by the following claims.

What is claimed is:

1. An abdominal binder assembly for securing a drainage bulb, the assembly comprising:
   an abdominal binder sheet of flexible material sized to cover substantially all of the patient's abdomen, the abdominal binder sheet comprising:
      a first surface comprising a loop-pile fabric which substantially covers an external side of the abdominal binder sheet, and
      a second surface including at least one region comprised of a hook fabric,
         wherein the hook fabric is configured to mate with the loop-pile fabric when the abdominal binder is wrapped around a patient's body; and
   a strip of material for securing across the body of the drainage bulb to the first surface on the external side of the abdominal binder sheet including a central portion, and first and second ends on two sides of the central portion, each of the first and second ends including hook fabric, the central portion for engaging the drainage bulb, and both the first and second ends for removably attaching to the loop-file fabric, wherein the strip of material is sized to cover only a portion of the drainage bulb and can be fully removed and reattached any location on to the loop-file fabric.

2. The abdominal binder of claim 1, further comprising an opening in the abdominal binder sheet configured to let through at least one drainage tube of the drainage bulb held on the external side of the abdominal binder sheet.

3. The abdominal binder of claim 2, wherein the opening includes a reinforced rim.

4. An abdominal binder assembly for securing a drainage bulb which has a flexible loop attached thereto, the assembly comprising:
   an abdominal binder sheet of flexible material sized to cover substantially all of the patient's abdomen, the abdominal binder sheet comprising:

a first surface comprising a loop-pile fabric which substantially covers an external side of the abdominal binder sheet, and a second surface including at least one region comprised of a hook fabric, wherein the hook fabric is configured to mate with the loop-pile fabric when the abdominal binder is wrapped around a patient's body; and a strip of material threaded through the flexible loop thereby for securing the drainage bulb to the first surface on the external side of the abdominal binder sheet, the strip of material including a central portion, and first and second ends on two sides of the central portion, each of the first and second ends including hook fabric and both for removably attaching to any location on the loop-file fabric, and the central portion for engaging the flexible loop, wherein the strip of material can be fully removed and reattached to the loop-file fabric.

5. The abdominal binder of any of claims 1-4, wherein the strip of material includes a tab configured to secure the drainage bulb to the first surface on the external side of the abdominal binder sheet.

6. The abdominal binder of claim 5, wherein the strip of material includes a single piece of hook material, the tab being cut from the single piece of hook material.

7. An abdominal binder assembly for securing a drainable bulb, the abdominal binder assembly comprising:
    an abdominal binder sheet of flexible material, comprising:
        a first surface comprising a loop-pile fabric which substantially covers an external side of the abdominal binder sheet, and
        a second surface including at least one region comprised of a hook fabric, wherein the hook fabric is configured to mate with the loop-pile fabric when the abdominal binder is wrapped around a patient's abdomen; and
        a second sheet of material including at least a piece of hook fabric, the second sheet of material sized to cover across the body of the drainage bulb and removably secure the drainage bulb to the loop-file fabric when the abdominal binder is secured to a patient,
    wherein the abdominal binder sheet is sized to cover substantially all of the patient's abdomen and the second sheet of material can be fully removed and reattached any location on to the loop-file fabric.

8. The abdominal binder assembly of claim 7, further comprising an opening in the abdominal binder sheet configured to let through a drainage tube of the drainage bulb held on the external side of the abdominal binder sheet.

9. The abdominal binder assembly of claim 8, wherein the opening includes a reinforced rim.

10. The abdominal binder assembly of claim 7, wherein the second sheet of material is sized to cover and secure at least two drainage bulbs to the first surface on the external side of the abdominal binder sheet when the abdominal binder is secured to a patient.

11. A method of providing abdominal support to a patient, comprising:
    securing an abdominal binder sheet of soft, flexible material around the abdomen of the patient by wrapping the abdominal binder sheet around the abdomen such that a first surface of the abdominal binder sheet, which is on an external side of the abdomen binder sheet and which comprises a loop-pile fabric substantially covering the first surface, contacts a second surface of the abdominal binder sheet including at least one region which comprises a hook fabric, wherein the abdominal binder sheet is sized to cover substantially all of the patient's abdomen; and
    securing a drainage bulb to the first surface on the external side of the abdominal binder sheet by placing a central portion of a strip of material over at least a portion of and across the body of the drainage bulb and removably attaching to the loop-file fabric both first and second ends of the strip of material which are located on two sides of the central portion and include hook fabric, wherein the strip of material is sized to cover only a portion of the drainage bulb and can be fully removed and reattached to the loop-file fabric.

12. The method of claim 11, wherein the first and second ends of the strip of material include hook type material.

13. The method of claim 12, wherein the strip of hook type material includes one or more tabs, and the securing the drainage bulb includes using one of the one or more tabs.

14. The method of claim 11, further including providing an opening in the abdominal binder sheet, the opening configured to let through a drainage tube of the drainage bulb.

15. The method of claim 14, further including passing the drainage tube of the drainage bulb through the opening in the abdominal binder sheet.

16. A method of providing abdominal support to a patient, comprising:
    securing an abdominal binder sheet of soft, flexible material around the abdomen of the patient by wrapping the abdominal binder sheet around the abdomen such that a first surface of the abdominal binder sheet, which is on an external side and which comprises a loop-pile fabric substantially covering the first surface, contacts a second surface of the abdominal binder sheet including at least one region which comprises a hook fabric, wherein the abdominal binder sheet is sized to cover substantially all of the patient's abdomen; and
    securing a drainage bulb to the first surface on the external side of the abdominal binder sheet by threading a strip of material through a loop attached to the drainage bulb, and removably attaching to the loop-file fabric both first and second ends of the strip of material which are located on two sides of a central portion of the strip of material and which include hook fabric such that the strip of material can be fully removed and reattached any location on to the loop-file fabric.

17. The method of claim 16, further including providing an opening in the abdominal binder sheet, the opening configured to let through a drainage tube of the drainage bulb.

18. The method of claim 17, further including passing the drainage tube of the drainage bulb through the opening in the abdominal binder sheet.

\* \* \* \* \*

UNITED STATES PATENT AND TRADEMARK OFFICE
CERTIFICATE OF CORRECTION

PATENT NO. : 8,066,657 B2  Page 1 of 1
APPLICATION NO. : 12/020971
DATED : November 29, 2011
INVENTOR(S) : Allison Frazer It is certified that error appears in the above-identified patent and that said Letters Patent is hereby corrected as shown below:

Claim 1, column 6, line 52, "loop-file" should read -- loop-pile --.

Claim 1, column 6, line 55, "loop-file" should read -- loop-pile --.

Claim 4, column 7, line 14, "loop-file" should read -- loop-pile --.

Claim 4, column 7, line 17, "loop-file" should read -- loop-pile --.

Claim 7, column 7, line 38, "loop-file" should read -- loop-pile --.

Claim 7, column 7, line 43, "loop-file" should read -- loop-pile --.

Claim 11, column 8, line 14, "loop-file" should read -- loop-pile --.

Claim 11, column 8, line 19, "loop-file" should read -- loop-pile --.

Claim 16, column 8, line 46, "loop-file" should read -- loop-pile --.

Claim 16, column 8, line 51, "loop-file" should read -- loop-pile --.

Signed and Sealed this
Twenty-fifth Day of September, 2012

David J. Kappos
*Director of the United States Patent and Trademark Office*